US006759533B2

(12) United States Patent
Busacca et al.

(10) Patent No.: US 6,759,533 B2
(45) Date of Patent: Jul. 6, 2004

(54) PROCESS AND INTERMEDIATES FOR MAKING NON-NUCLEOSIDE HIV-1 REVERSE TRANSCRIPTASE INHIBITORS

(75) Inventors: Carl A. Busacca, Poughkeepsie, NY (US); Magnus C. Eriksson, Brewster, NY (US); Ji-Young Kim, Ann Arbor, MI (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 10/465,754

(22) Filed: Jun. 19, 2003

(65) Prior Publication Data

US 2004/0002489 A1 Jan. 1, 2004

Related U.S. Application Data

(60) Provisional application No. 60/391,979, filed on Jun. 28, 2002, and provisional application No. 60/434,052, filed on Dec. 17, 2002.

(51) Int. Cl.[7] ............................................. C07D 471/14
(52) U.S. Cl. ........................................................ 540/495
(58) Field of Search ........................................... 540/495

(56) References Cited

U.S. PATENT DOCUMENTS

| 6,057,456 A | 5/2000 | Hartwig et al. |
| 6,072,073 A | 6/2000 | Kawatsura et al. |
| 6,307,087 B1 | 10/2001 | Buchwald et al. |
| 6,420,359 B1 | 7/2002 | Simoneau |

OTHER PUBLICATIONS

Simoneau, B., "Non–Nucleoside Reverse Transcriptase Inhibitors"; US patent application Publication No. 2002/0028807 A1; Mar. 7, 2002.
Kowalczyk, B., "Synthesis of dihalophenylacetic acids using aromatic nucleophilic substitution strategy"; Synthesis; vol. 12; 1997; pp. 1411–1414.
Moradi, W. A. et al; "Palladium–Catalyzed alpha–Arylation of Esters"; J. Am Chem. Soc. 2001, 123, pp. 7996–8002.

Fox, J. M. et al; "Highly Active and Selective Catalysts for the Formation of alpha–Aryl Ketones"; J. Am. Chem. Soc. 2000, 122, pp. 1360–1370.

*Primary Examiner*—Bruck Kifle
(74) *Attorney, Agent, or Firm*—Robert P. Raymond; Alan R. Stempel; Mary-Ellen M. Devlin

(57) ABSTRACT

A process and novel intermediates for making compounds of the formula I:

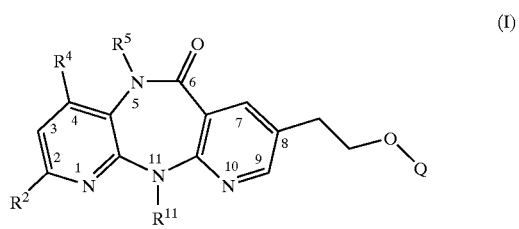

wherein:
$R^2$ is selected from the group consisting of H, F, Cl, $C_{1-4}$ alkyl, $C_{3-4}$ cycloalkyl and $CF_3$;
$R^4$ is H or Me;
$R^5$ is H, Me or Et, with the proviso that $R^4$ and $R^5$ are not both Me, and if $R^4$ is Me then $R^5$ cannot be Et;
$R^{11}$ is Me, Et, cyclopropyl, propyl, isopropyl, or cyclobutyl; and
Q is selected from the group consisting of:

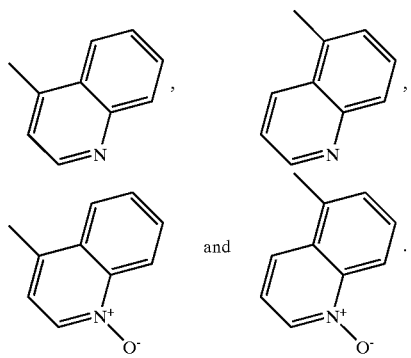

8 Claims, No Drawings

PROCESS AND INTERMEDIATES FOR MAKING NON-NUCLEOSIDE HIV-1 REVERSE TRANSCRIPTASE INHIBITORS

RELATED APPLICATIONS

Benefit of U.S. provisional application Serial No. 60/391,979 filed on Jun. 28, 2002 and provisional application Serial No. 60/434,052 filed on Dec. 17, 2002 are hereby claimed.

TECHNICAL FIELD OF THE INVENTION

The invention relates to a novel process and novel intermediates for the synthesis of certain non-nucleoside reverse transcriptase inhibitors.

BACKGROUND OF THE INVENTION

The disease known as acquired immune deficiency syndrome (AIDS) is caused by the human immunodeficiency virus (HIV), particularly the strain known as HIV-1. In order for HIV to be replicated by a host cell, the information of the viral genome must be integrated into the host cell's DNA. However, HIV is a retrovirus, meaning that its genetic information is in the form of RNA. The HIV replication cycle, therefore, requires a step of transcription of the viral genome (RNA) into DNA. The transcription of the viral RNA into DNA is accomplished by an enzyme that has been aptly dubbed reverse transcriptase (RT). The HIV virion includes a copy of RT along with the viral RNA.

Reverse transcriptase has three known enzymatic functions. It acts as an RNA-dependent DNA polymerase, as a ribonuclease, and as a DNA-dependent DNA polymerase. Acting as an RNA-dependent DNA polymerase, RT transcribes a single-stranded DNA copy of the viral RNA. Acting as a ribonuclease, RT destroys the original viral RNA, and frees the DNA just produced from the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds that inhibit the enzymatic functions of HIV-1 reverse transcriptase will inhibit replication of HIV-1 in infected cells. Such compounds are useful in the prevention or treatment of HIV-1 infection in human subjects, as demonstrated by known RT inhibitors such as 3'-aziod-3'-deoxythymidine (AZT), 2',3'-dideoxyinosine (ddI), 2',3'-dideoxycytidine (ddC), d4T, 3TC, nevirapine, delavirdine, efavirenz and abacavir, the RT inhibitors thus far approved as drugs for use in the treatment of HIV infection.

As with any antiviral therapy, use of RT inhibitors in the treatment of HIV infection eventually leads to a virus that is less sensitive to the given drug. Resistance (reduced sensitivity) to these drugs is the result of mutations that occur in the reverse transcriptase segment of the pol gene. Several mutant strains of HIV have been characterised, and resistance to known therapeutic agents is due to mutations in the RT gene. Some of the most commonly observed mutant clinically are: the Y181C mutant, in which a tyrosine Y, at codon 181, has been mutated to a cysteine C residue, and K103N where the lysine K at position 103 has been replaced by asparagine N. Other mutants which emerge with increasing frequency during treatment with known antivirals include the single mutants V106A, G190A, Y188C, and P236L: and the double mutants K103N/Y181C, K013N/P225H, K103N/V108I and K103N/L100I.

As therapy of HIV infection using antivirals continues, the emergence of new resistant strains is expected to increase. There is therefore an ongoing need for new inhibitors of RT, with different patterns of effectiveness against the various mutants.

Of particular relevance to the present invention are the HIV-RT inhibitors disclosed by U.S. Pat. No. 6,420,359. These compounds, which are all dipyrido[3,2-b:2',3'-e][1,4]diazepin-6-ones bearing a 2-(quinolinyl)oxyethyl or a 2-(1-oxido-quinolinyl)oxyethyl group in the 8-position, have enhanced activity against certain clinically significant mutant strains of HIV-1. It is the object of the present invention to provide an alternative method for making the compounds disclosed by U.S. Pat. No. 6,420,359.

SUMMARY OF THE INVENTION

The invention provides an improved process for making compounds of the general formula I:

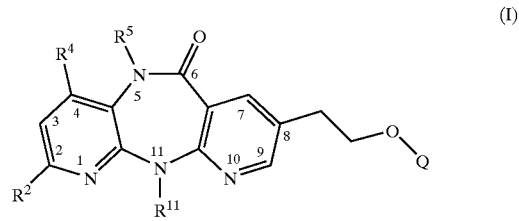

wherein:

$R^2$ is selected from the group consisting of H, F, Cl, $C_{1-4}$ alkyl, $C_{3-4}$ cycloalkyl and $CF_3$;

$R^4$ is H or Me;

$R^5$ is H, Me or Et, with the proviso that $R^4$ and $R^5$ are not both Me, and if $R^4$ is Me then $R^5$ cannot be Et;

$R^{11}$ is Me, Et, cyclopropyl, propyl, isopropyl, or cyclobutyl; and

Q is selected from the group consisting of:

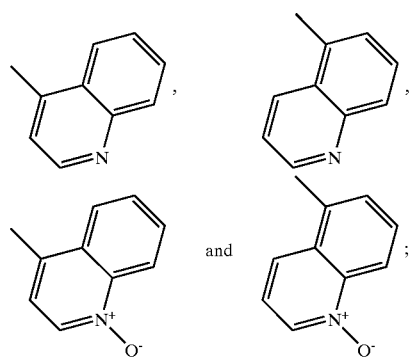

as well as pharmaceutically acceptable salts thereof.

DETAILED DESCRIPTION OF THE INVENTION

The synthetic method of the invention commences from a starting compound of the formula II

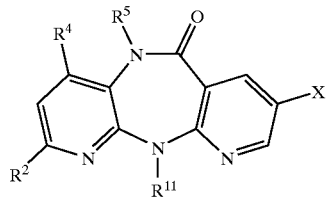

(II)

wherein $R^2$, $R^4$, $R^5$ and $R^{11}$ are as defined above with respect to compounds of the formula I and wherein X is a chlorine, iodine, or bromine, or a fluorosulfonate moiety selected from the group consisting of —$OSO_2F$ and —$OSO_2(CF_2)_nCF_3$ wherein n is an integer between 0 and 10. Processes for making starting compounds of the formula II wherein X is bromine are described in U.S. Pat. No. 6,420,359. Compounds wherein X is other than bromine can be made by analogous methods which will be readily apparent to those of ordinary skill in the art.

It is preferred to use a compound of the formula II wherein X is bromine.

The starting compound of the formula II initially undergoes a palladium-catalyzed coupling reaction wherein it is caused to arylate a malonate or malonate surrogate of the formula III

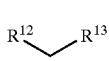

(III)

wherein,
$R^{12}$ is a cyano group or a group of the formula —$COOR^{14}$, wherein $R^{14}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl, and $R^{13}$ is a cyano group, a group of the formula —$COOR^{15}$ (wherein $R^{15}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl), a group of the formula —$SO_2R^{16}$ (wherein $R^{16}$ is a $C_{1-4}$-alkyl group, phenyl, furyl, pyridyl or benzyl), a group of the formula —$P(O)(OR^{17})_2$ (wherein $R^{17}$ is phenyl, furyl or pyridyl) or a group of the formula —$SOR^{18}$ (wherein $R^{18}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl).

It is preferred to employ a malonate surrogate of the formula III

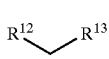

(III)

wherein,
$R^{12}$ is a cyano group or a group of the formula —$COOR^{14}$, wherein $R^{14}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl; and $R^{13}$ is a cyano group, a group of the formula —$SO_2R^{16}$ (wherein $R^{16}$ is a $C_{1-4}$-alkyl group, phenyl, furyl, pyridyl or benzyl), a group of the formula —$P(O)(OR^{17})_2$ (wherein $R^{17}$ is phenyl, furyl or pyridyl) or a group of the formula —$SOR^{18}$ (wherein $R^{18}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl).

The reaction of the compounds of the formulas II and III takes place in an organic solvent, in the presence of a palladium catalyst, a suitable ligand and strong base. Suitable solvents are, by way of non-limiting example, toluene, ethylbenzene, xylene, DMF, DMA, NMP, dioxane and THF, with toluene being preferred. Virtually any palladium catalyst may be used, such as, for example, $Pd(OAc)_2$, $PdCl_2$, $Pd_2dba_3$ and Pd on carbon, with $Pd(OAc)_2$ being preferred. Suitable bases are, for example, the metal hydrides such as, for example, NaH, the metal alkoxides such as, for example, t-BuOK, t-BuONa and Na-tert-amylate, the metal carbonates such as, for example, $Na_2CO_3$, $K_2CO_3$ and $CS_2CO_3$, with NaH being preferred, and the metal phosphates such as, for example, $K_3PO_4$. When the reactant of the formula III is a malonate (compounds wherein $R^{12}$ and $R^{13}$ are both carboxylic acid ester groups) then suitable ligands will be t-$Bu_3P$, one of the ligands described and claimed in U.S. Pat. No. 6,307,087, or a ferrocenyl phosphine such as described in U.S. Pat. Nos. 6,057,456 and 6,072,073. When the reactant of the formula III is not a malonate, but rather a malonate surrogate (a compound wherein $R^{12}$ and $R^{13}$ are not both carboxylic acid ester groups) the above-mentioned ligands may be employed and, in addition, a triarylphosphine such as, by way of non-limiting example, $PPh_3$, o-$Tol_3P$, p-$Tol_3P$ and o-$Fur_3P$ may also be employed. In such case the preferred ligand is $PPh_3$.

The reaction is preferably carried out at elevated temperature, more preferably in the range between about 50 and 150° C.

The above described reaction, which couples the compounds of the formulas II and III, yields an intermediate of the formula IV

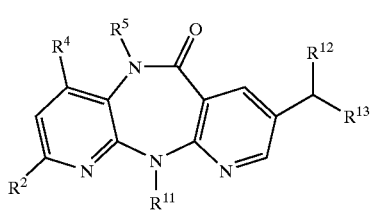

(IV)

wherein $R^2$, $R^4$, $R^5$, $R^{11}$, $R^{12}$ and $R^{13}$ are as defined above.

Isolation of the intermediate of the formula IV before going on to the next process step is optional. It has been found that a one pot synthesis wherein the intermediate IV is not isolated is quite convenient. If the intermediate IV is not isolated and the residual base is a metal hydride, such as NaH, then it is advisable to quench the base with an agent such as isopropyl alcohol before going on to the next step.

If the intermediate of the formula IV contains sulfur or phosphorus (because $R^{13}$ in the reactant of the formula III was a group of the formula —$SO_2R^{15}$ or —$P(O)(OR^{16})_2$) then the next process step is a reductive cleavage of the sulfur or phosphorus-containing group. Methods for performing such reductive cleavage will be well known to those of ordinary skill in the art. For example, this might be accomplished by the use of Raney nickel or a dissolving metal reaction.

Subsequent to the reductive cleavage or, if the intermediate of formula IV does not contain sulfur or phosphorus, the intermediate of the formula IV is next hydrolyzed to yield a further intermediate of the formula V

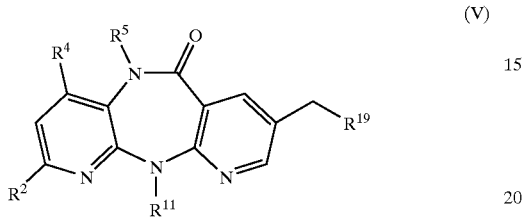

(V)

wherein $R^2$, $R^4$, $R^5$ and $R^{11}$ are as defined above and $R^{19}$ is —COOH or, if the reactant of formula III was a malonate and mild hydrolysis conditions are employed, $R^{19}$ may additionally be a group of the formula —COOR$^{14}$ wherein $R^{14}$ is as described above. The hydrolysis may be performed in a manner that will be conventional and readily apparent to those of ordinary skill in the art. For example, it may be accomplished using an aqueous base, such as NaOH, preferably at ambient temperature or above.

The intermediates of the formulas IV and V are believed to be novel and constitute a part of the invention.

Isolation of the intermediate V before going on to the next step is preferred.

Next, the carboxylic acid or ester intermediate of the formula V is reduced to yield an alcohol of the formula VI

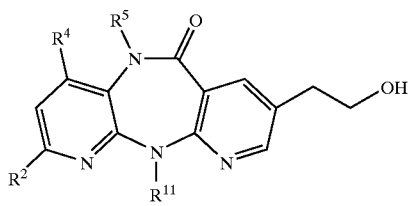

(VI)

wherein $R^2$, $R^4$, $R^5$ and $R^{11}$ are as defined above. Reduction is carried out in a conventional manner that will be readily apparent to those of ordinary skill in the art. Regardless of whether the intermediate of the formula V is an acid or an ester, reduction may be accomplished using boranes, borohydrides or other metal hydrides or dissolving metal reductants, with boranes being preferred for the acids and borohydrides being preferred for the esters. If a borane is to be employed it is preferred to make it in situ from a borohydride, such as sodium borohydride, and an electrophilic reagent such as, for example HCl.

Finally, the alcohol of formula VI is converted to the final product of the formula I by a condensation reaction with a reactant of the formula

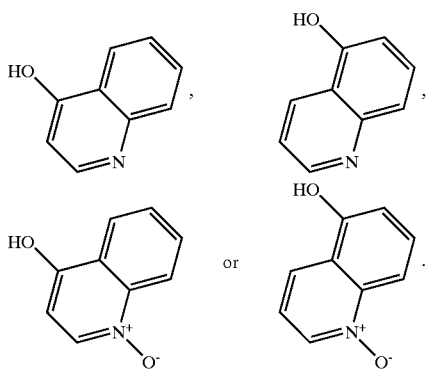

This condensation may be accomplished in the manner described in U.S. Pat. No. 6,420,359.

The nature and scope of the invention will be better appreciated from the following examples.

EXAMPLE 1

Arylation of Malononitrile: Formation of Compound of Formula IV Where R2=R4=H, R5= Me, R11=ethyl, and R12=R13=CN A flask was charged with 10.0 g tricyclic bromide (compound of formula II where $R^2$=$R^4$=H, R5=Me, R11=ethyl, and X=Br; 30 mmol, 1 eq.), 0.95 g triphenylphosphine (3.6 mmol, 0.12 eq.), 0.55 g Pd$_2$dba$_3$ (0.6 mmol, 0.04 eq.), and 40 mL 1,4-dioxane. To this mixture was then added 2.16 g sodium hydride (90 mmol, 3 eq.) in portions over 15 minutes, using 40 mL 1,4-dioxane to complete the addition. A solution of 2.57 g malononitrile (39 mmol, 1.3 eq.) in 5 mL 1,4-dioxane was then added, and the mixture heated to 90° C. After 18 h the mixture was cooled to ambient temperature and cautiously quenched with 100 mL of sat'd ammonium chloride solution. The pH was then adjusted to 6 with 1N HCl, and the mixture extracted with dichloromethane. The organic solution was dried (magnesium sufate), and the solvents removed in vacuo to give 7.03 g (73%) of the product as a brown oil. NMR and MS showed the desired product (Compound of Formula IV where $R^2$=$R^4$=H, $R^5$=Me, $R^{11}$=ethyl, and $R^{12}$=$R^{13}$=CN).

EXAMPLE 2

Arylation of Diethylmalonate: Formation of Compound of Formula IV Where $R^2$=$R^4$=H, $R^5$= Me, $R^{11}$=Ethyl, and $R^{12}$=$R^{13}$=CO$_2$Et A 500 ml two neck round bottom flask fitted with mechanical stirrer, reflux condenser and thermocouple was purged with argon for 20 minutes, then 404 mg Pd(OAc)$_2$ (1.80 mmol, 0.03 eq.), 1.08 g 2-(di-t-butylphosphino) biphenyl (3.60 mmol, 0.06 eq.), and 20.0 g tricyclic bromide (compound of formula II where R2=R4=H, R5=Me, R11=ethyl, and X=Br; (60.0 mmol, 1 eq.) were charged. To this mixture in an inerted flask was then added 25.5 g K$_3$PO$_4$ (120 mmol, 2 eq.), 100 mL PhMe, and 13.8 mL diethylmalonate (90.0 mmol, 1.5 eq.) were then added. The stirred suspension was placed in an oil bath and heated at reflux under nitrogen for 24 h until the bromide was consumed by HPLC. The reaction mixture was cooled to room temperature and diluted with water (150 ml) and toluene (50 ml) was added. The mixture was stirred for 1 h at room temperature until all solids had dissolved. The two-phase solution was then transferred to a separatory funnel and the layers were separated. The aqueous layer was extracted with toluene (50 ml). The combined organic layers were filtered through a pad of Celite and concentrated under vacuum to give a viscous oil, which was evaporated to dryness to furnish an orange solid. Silica gel chromatography (1:1 EtOAc:Hex) provided 20.5 g pure malonate adduct (compound of formula IV where $R^2=R^4=H$, $R^5=Me$, $R^{11}=$ethyl, and $R^{12}=R^{13}=CO_2Et$), (83%), as a colorless solid, m.p. 122–123° C.; $^1H$ NMR (400 MHz, CDCl$_3$) δ: 8.38 (d, J=2.5 Hz, 1H), 8.19 (dd, J=1.5, 4.6 Hz, 1H), 8.16 (d, J=2.4 Hz, 1H), 7.47 (dd, J==1.5, 8.0 Hz, 7.09 (dd, J=4.7, 8.0 Hz, 1H), 4.56 (s, 1H), 4.20 (m, 6H), 3.49 (s, 3H), 1.25 (t, J=7.1 Hz, 9H). $^{13}C$ NMR (100 MHz, CDCl$_3$) δ: 167.30 (s), 167.23 (s), 159.31 (s), 154.50 (s), 151.18 (d), 144.34 (d), 141.93 (d), 131.63 (s), 130.74 (d), 123.52 (s), 120.57 (s), 119.78 (d), 62.17 (t), 54.80 (d), 41.24 (t), 37.30 (q), 13.96 (q), 13.58 (q). Anal. Calcd for $C_{21}H_{24}N_4O_5$: C, 61.15; H, 5.87; N, 13.58. Found: C, 61.14; H, 5.66; N, 13.51.

EXAMPLE 3

Arylation of Isopropylcyanoacetate and Formation of Compound of Formula V Where $R^2=R^4=H$, $R^5=Me$, $R^{11}=$ethyl, and $R^{19}=CO_2H$ An inerted 800 L reactor was charged with 12.0 Kg 60% NaH/oil (300 mol, 2.5 eq.), 0.27 Kg Pd(OAc)$_2$ (1.2 mol, 0.01 eq.), 1.26 Kg PPh$_3$ (4.8 mol, 0.04 eq.), and 40 Kg tricyclic bromide (compound of formula II where $R^2=R^4=H$, $R^5=Me$, $R^{11}=$ethyl, and X=Br; 120 mol, 1 eq.). The reactor was again inerted, then 70 Kg of PhMe was charged, and the mixture heated to 60° C. To this mixture was then added a solution of 17.4 L cyanoisopropylacetate (138 mol, 1.15 eq.) in 20 L PhMe via metering pump at a fixed rate over 2 hours (Caution: H$_2$ gas evolution). The reactor contents were then heated to 100° C. and maintained there for 1.5 hours. HPLC of an aliquot showed the arylation was complete to compound of formula IV where $R^2=R^4=H$, $R^5=Me$, $R^{11}=$ethyl, $R^{12}=CN$ and $R^{13}=CO_2iPr$. The mixture was then cooled to 35° C. and quenched by the addition of 19 Kg isopropanol (308 mol, 2.6 eq.) over 20 minutes (Caution: H$_2$ gas evolution). 438 Kg 1M NaOH solution (417 mol, 3.5 eq.) was then added, and the mixture heated to 80° C. and maintained there for 8 hours. HPLC of an aliquot showed the hydrolysis was complete to the desired carboxylic acid. The mixture was cooled to 25° C. and the phases separated. The upper phase was discarded to waste, while the lower aqueous phase was returned to the reactor. 218 Kg EtOAc was then charged and the mixture agitated for 15 minutes, then the phases were allowed to separate. The lower aqueous phase was returned to the reactor and cooled to 10° C. To this mixture was then slowly added 6N H$_2$SO$_4$ with continuous monitoring of pH until a final pH of 3.3 was achieved: this required 133 Kg of H$_2$SO$_4$ solution. The resulting slurry was then warmed to 25° C. and maintained there for 1 hour. The batch was then centrifuged and washed twice with 40 Kg H$_2$O. The solid was then dried at full vacuum at 40° C. until LOD<1% to give 36.0 Kg of the carboxylic acid (compound of formula V where $R^2=R^4=H$, $R^5=Me$, $R^{11}=$ethyl, and $R^{19}=CO_2H$; 96%), as an off white solid. Mp 226–228° C.; $^1H$ NMR (500 MHZ, DMSO) δ: 12.47 (s, 1H), 8.32 (d, J=2.0 Hz, 1H), 8.20 (dd, J=4.6, 1.5 Hz, 1H), 7.96 (d, J=2.3 Hz, 1H), 7.81 (dd, J=8.0, 1.6 Hz, 1H), 7.24 (m, J=4.6, 8.0 Hz, 1H), 4.08 (q, J=7.0 Hz, 2H), 3.63 (s, 3H), 3.43 (s, 3H), 1.17 (t, J=7.0 Hz, 3H). $^{13}C$ NMR (125 MHz, DMSO) δ: 172.22 (s), 166.26 (s), 157.47 (s), 153.96 (s), 151.32 (d), 144.06 (d), 141.59 (d), 131.72 (d), 131.14 (s), 126.01 (s), 120.28 (d), 120.12 (s), 40.45 (t), 36.74 (q), 36.34 (t), 13.42 (q). Anal. Calcd for $C_{16}H_{16}N_4O_3$: C, 61.53; H, 5.16; N, 17.94. Found: C, 61.28; H, 4.94; N, 17.56.

EXAMPLE 4

Arylation of Methylphenylsulfonyl Acetate: Formation of Compound of Formula IV Where $R^2=R^4=H$, $R^5=Me$, $R^{11}=$Ethyl, $R^{12}=CO_2Me$ and $R^{13}=SO_2Ph$ A flask was charged with 165 mg Pd$_2$dba$_3$ (0.18 mmol, 0.02 eq.), 577 mg triphenylphosphine (2.2 mmol, 0.12 eq.), and 45 mL 1,4-dioxane. After stirring in an inert atmosphere for 15 minutes, 647 mg NaH (27 mmol, 3 eq.) was added in portions. To this mixture was then added 3.00 g tricyclic bromide (compound of formula II where $R^2=R^4=H$, $R^5=Me$, $R^{11}=$ethyl, and X=Br; 9.00 mmol, 1 eq.), followed by 2.50 g (11.7 mmol, 1.3 eq.) of methylphenylsulfonyl acetate. The mixture was then heated at 60° C for 18 h, cooled to ambient temperature and quenched by the addition of 0.5 mL H$_2$O. The dioxane was removed in vacuo to give the crude product as a grey solid, 3.5 g (~90%). NMR and MS indicated the desired arylation product (Compound of Formula IV where $R^2=R^4=H$, $R^5=Me$, $R^{11}=$ethyl, $R^{12}=CO_2Me$ and $R^{13}=SO_2Ph$).

EXAMPLE 5

Arylation of Diethylphosphonyl Acetonitrile: Formation of Compound of Formula IV Where $R^2=R^4=H$, $R^5=Me$, $R^{11}=$Ethyl, $R^{12}=CN$ and $R^{13}=P(O)(OEt)_2$ A flask was charged with 1.00 g tricyclic bromide (compound of formula II where $R^2=R^4=H$, $R^5=Me$, $R^{11}=$ethyl, and X=Br; 3.00 mmol, 1 eq.), 55 mg Pd$_2$dba$_3$ (0.06 mmol, 0.02 eq.), 95 mg triphenylphosphine (0.36 mmol, 0.12 eq.), and 0.69 g diethylphosphonyl acetonitrile (3.90 mmol, 1.3 eq.). To this mixture was then added 15 mL 1,4-dioxane, followed by 216 mg NaH (9.00 mmol, 3 eq.). The resulting mixture was then heated at 70° C. for three hours. The mixture was cooled to ambient temperature and quenched by the cautious addition of 25 mL H$_2$O, and 20 mL dichloromethane was added. The pH was then adjusted to 2.5 with 1N aq. HCl and diluted with additional H$_2$O (25 mL) and dichloromethane (25 mL). The phases were then separated and the organic phase concentrated to a brown oil. The oil was then triturated with 10 mL t-butylmethyl ether to give a precipitate of the product, which was filtered to give 0.95 g product as an off white solid. NMR and MS indicated the desired arylation product (Compound of Formula IV where $R^2=R^4=H$, $R^5=Me$, $R^{11}=$ethyl, $R^{12}=CN$ and $R^{13}=P(O)(OEt)_2$).

What is claimed is:

1. A process for making a compound of the formula I:

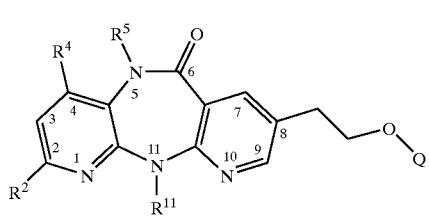
(I)

wherein:
$R^2$ is selected from the group consisting of H, F, Cl, $C_{1-4}$ alkyl, $C_{3-4}$ cycloalkyl and $CF_3$;
$R^4$ is H or Me;
$R^5$ is H, Me or Et, with the proviso that $R^4$ and $R^5$ are not both Me, and if $R^4$ is Me then $R^5$ cannot be Et;
$R^{11}$ is Me, Et, cyolopropyl, propyl, isopropyl, or cyclobutyl; and
Q is selected from the group consisting of:

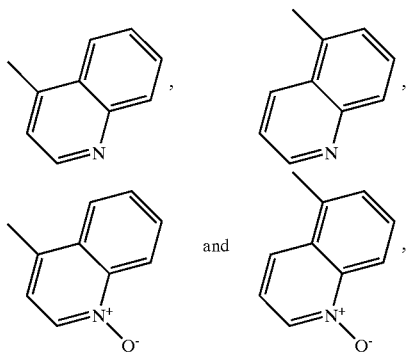

which process comprises the following steps:
(a) reacting a starting compound of the formula II

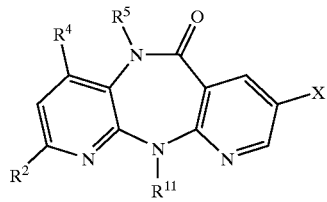
(II)

wherein $R^2$, $R^4$, $R^5$ and $R^{11}$ are as hereinbefore defined with respect to the compound of the formula I and wherein X is a chlorine, iodine, or bromine, or a fluorosulfonate moiety selected from the group consisting of $-OSO_2F$ and $-OSO_2(CF_2)_nCF_3$ wherein n is an integer between 0 and 10, with a malonate or malonate surrogate of the formula III

(III)

wherein,
$R^{12}$ is a cyano group or a group of the formula $-COOR^{14}$, wherein $R^{14}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl, and $R^{13}$ is a cyano group, a group of the formula $-COOR^{15}$ (wherein $R^{15}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl), a group of the formula $-SO_2R^{16}$ (wherein $R^{16}$ is a $C_{1-4}$-alkyl group, phenyl, furyl, pyridyl or benzyl), a group of the formula $-P(O)(OR^{17})_2$ (wherein $R^{17}$ is phenyl, furyl or pyridyl) or a group of the formula $-SOR^{18}$ (wherein $R^{18}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl), in an organic solvent, in the presence of a palladium catalyst, a suitable ligand and strong base,
to yield an intermediate of the formula IV

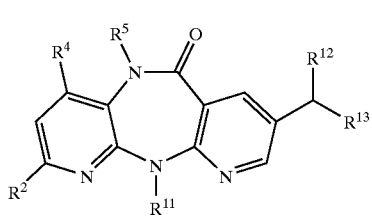
(IV)

wherein $R^2$, $R^4$, $R^5$, $R^{11}$, $R^{12}$ and $R^{13}$ are as hereinbefore defined in this claim;

(b) reductively cleaving the sulfur or phosphorus-containing group, if the intermediate of the formula IV contains a sulfur or phosphorus-containing group;

(c) hydrolyzing the intermediate of the formula IV to yield a further intermediate of the formula V

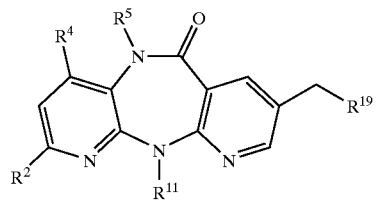
(V)

wherein $R^2$, $R^4$, $R^5$ and $R^{11}$ are as hereinbefore defined in this claim and $R^{19}$ is $-COOH$ or, if the reactant of formula III was a malonate and mild hydrolysis conditions are employed, wherein $R^{19}$ may additionally be a group of the formula $-COOR^{14}$ wherein $R^{14}$ is as hereinbefore defined in this claim;

(d) reducing the carboxylic acid or ester intermediate of the formula V to yield an alcohol of the formula VI

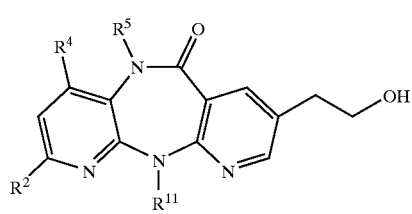
(VI)

wherein $R^2$, $R^4$, $R^5$ and $R^{11}$ are as hereinbefore defined in this claim; and (e) condensing the alcohol of formula VI with a reactant of the formula

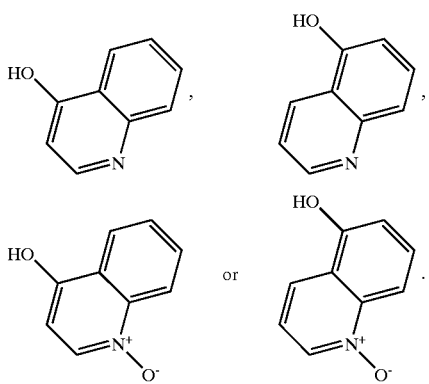

to yield the final product of the formula I.

2. A process for making a compound of the formula IV

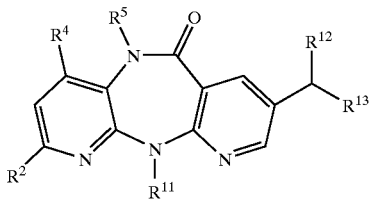

wherein:

$R^2$ is selected from the group consisting of H, F, Cl, $C_{1-4}$ alkyl, $C_{3-4}$ cycloalkyl and $CF_3$, $R^4$ is H or Me, $R^5$ is H, Me or Et, with the proviso that $R^4$ and $R^5$ are not both Me, and if $R^4$ is Me then $R^5$ cannot be Et, $R^{11}$ is Me, Et, cyclopropyl, propyl, isopropyl, or cyclobutyl, $R^{12}$ is a cyano group or a group of the formula —$COOR^{14}$, wherein $R^{14}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl, and $R^{13}$ is a cyano group, a group of the formula —$COOR^{15}$ (wherein $R^{14}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl), a group of the formula —$SO_2R^{16}$ (wherein $R^{16}$ is a $C_{1-4}$-alkyl group, phenyl, furyl, pyridyl or benzyl), a group of the formula —$P(O)(OR^{17})_2$ (wherein $R^{17}$ is phenyl, furyl or pyridyl) or a group of the formula —$SOR^{18}$ (wherein $R^{18}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl), which process comprises the following steps:

(a) reacting a starting compound of the formula II

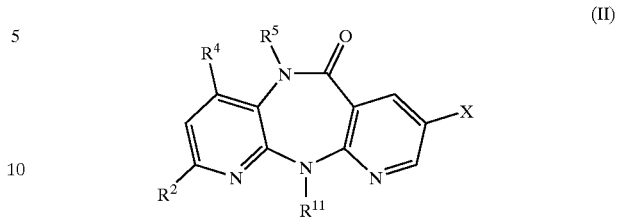

wherein $R^2$, $R^4$, $R^5$ and $R^{11}$ are as hereinbefore defined in this claim and wherein X is a chlorine, iodine, or bromine, or a fluorosulfonate moiety selected from the group consisting of —$OSO_2F$ and —$OSO_2(CF_2)_nCF_3$ wherein n is an integer between 0 and 10, with a malonate or malonate surrogate of the formula III

wherein, $R^{12}$ is a cyano group or a group of the formula —$COOR^{14}$, wherein $R^{14}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl, and $R^{13}$ is a cyano group, a group of the formula —$COOR^{15}$ (wherein $R^{14}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl), a group of the formula —$SO_2R^{16}$ (wherein $R^{16}$ is a $C_{1-4}$-alkyl group, phenyl, furyl, pyridyl or benzyl), a group of the formula —$P(O)(OR^{17})_2$ (wherein $R^{17}$ is phenyl, furyl or pyridyl) or a group of the formula —$SOR^{18}$ (wherein $R^{18}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl), in an organic solvent, in the presence of a palladium catalyst, a suitable ligand and strong base, to yield the compound of the formula IV.

3. A process for making a compound of the formula V

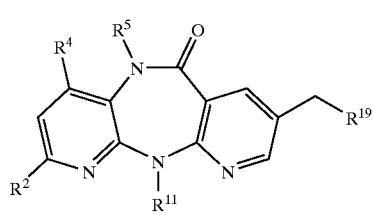

wherein:

$R^2$ is selected from the group consisting of H, F, Cl, $C_{1-4}$ alkyl, $C_{3-4}$ cycloalkyl and $CF_3$;

$R^4$ is H or Me;

$R^5$ is H, Me or Et, with the proviso that $R^4$ and $R^5$ are not both Me, and if $R^4$ is Me then $R^5$ cannot be Et;

$R^{11}$ is Me, Et, cyclopropyl, propyl, isopropyl, or cyclobutyl; and $R^{19}$ is —COOH or a group of the formula —$COOR^{14}$ wherein $R^{14}$ is a $C_{1-4}$-alkyl group, a $C_{1-4}$-alkyloxy- $C_{1-4}$-alkyl group group phenyl, naphthyl, thiophenyl, furyl, pyridyl, imidazole or benzyl;
which process comprises the following steps:
(a) reacting a starting compound of the formula II

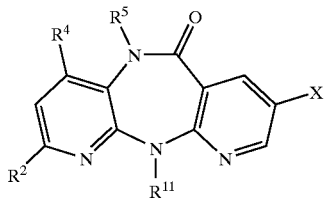

(II)

wherein $R^2$, $R^{4, R5}$ and $R^{11}$ are as hereinbefore defined in this claim and wherein X is a chlorine, iodine, or bromine, or a fluorosulfonate moiety selected from the group consisting of —OSO$_2$F and —OSO$_2$(CF$_2$)$_n$CF$_3$ wherein n is an integer between 0 and 10,
with a malonate or malonate surrogate of the formula III

(III)

wherein,
$R^{12}$ is a cyano group or a group of the formula —COOR$^{14}$, wherein $R^{14}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl, and
$R^{13}$ is a cyano group, a group of the formula —COOR$^{15}$ (wherein $R^{14}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl), a group of the formula —SO$_2$R$^{16}$ (wherein $R^{16}$ is a $C_{1-4}$-alkyl group, phenyl, furyl, pyridyl or benzyl), a group of the formula —P(O)(OR$^{17}$)$_2$ (wherein $R^{17}$ is phenyl, furyl or pyridyl) or a group of the formula —SOR$^{18}$ (wherein $R^{18}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl),
in an organic solvent, in the presence of a palladium catalyst, a suitable ligand and strong base,
to yield an intermediate of the formula IV

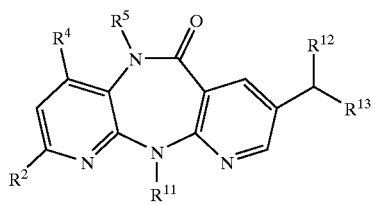

(IV)

wherein $R^2$, $R^4$, $R^5$, $R^{11}$, $R^{12}$ and $R^{13}$ are as hereinbefore defined in this claim;
(b) reductively cleaving the sulfur or phosphorus-containing group, if the intermediate of the formula IV contains a sulfur or phosphorus-containing group (because $R^{13}$ in the reactant of to formula III was a group of the formula —SO$_2$R$^{15}$ or —P(O)(OR$^{16}$)$_2$); and,
(c) hydrolyzing the intermediate of the formula IV to yield the compound of the formula V.

4. The process according to claim 3, wherein the reactant of the formula III is a malonate and the ligand employed is t-Bu$_3$P or a ferrocenyl phosphine.

5. The process according to claim 3, wherein the reactant of the formula III is a malonate surrogate and the ligand employed is t-Bu$_3$P a ferrocenyl phosphine or a triarylphosphine.

6. The process of claim 5 wherein the ligand is PPh$_3$, o-Tol$_3$P, p-Tol$_3$P or o-Fur$_3$P.

7. A compound of the formula IV

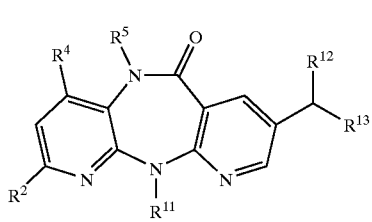

(IV)

wherein:

$R^2$ is selected from the group consisting of H, F, Cl, $C_{1-4}$ alkyl, $C_{3-4}$ cycloalkyl and CF$_3$;

$R^4$ is H or Me;

$R^5$ is H, Me or Et, with the proviso that $R^4$ and $R^5$ are not both Me, and if $R^4$ is Me then $R^5$ cannot be Et;

$R^{11}$ is Me, Et, cyclopropyl, propyl, isopropyl, or cyclobutyl;

$R^{12}$ is a cyano group or a group of the formula —COOR$^{14}$, wherein $R^{14}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl, and $R^{13}$ is a cyano group, a group of the formula —COOR$^{15}$ (wherein $R^{14}$ is a $C_{1-4}$-alkyl group, a $C_{1-4}$-alkyloxy-$C_{1-4}$alkyl group group phenyl, naphthyl, thiophenyl, furyl, pyridyl, imidazole or benzyl), a group of the formula —SO$_2$R$^{16}$ (wherein $R^{16}$ is a $C_{1-4}$-alkyl group, phenyl, furyl, pyridyl or benzyl), a group of the formula —P(O)(OR$^{17}$)$_2$ (wherein $R^{17}$ is phenyl, furyl or pyridyl) or a group of the formula —SOR$^{18}$ (wherein $R^{18}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl).

8. A compound of the formula V

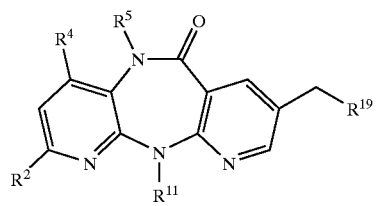

(V)

wherein:

$R^2$ is selected from the group consisting of H, F, Cl, $C_{1-4}$ alkyl, $C_{3-4}$ cycloalkyl and $CF_3$;

$R^4$ is H or Me;

$R^5$ is H, Me or Et, with the proviso that $R^4$ and $R^5$ are not both Me, and if $R^4$ is Me then $R^5$ cannot be Et;

$R^{11}$ is Me, Et, cyolopropyl, propyl, isopropyl, or cyclobutyl; and $R^{19}$ is —COOH or a group of the formula —COOR$^{14}$ wherein $R^{14}$ is a $C_{1-4}$-alkyl group, a $C_{1-4}$-alkyloxy-$C_{1-4}$-alkyl group group phenyl, naphthyl, thiophenyl, furyl, pyridyl, imidazole or benzyl.

* * * * *